(12) United States Patent
Katsnelson

(10) Patent No.: US 7,769,463 B2
(45) Date of Patent: Aug. 3, 2010

(54) MULTI-CHANNEL ELECTROSTIMULATION APPARATUS AND METHOD

(75) Inventor: Yakov Katsnelson, Weehawken, NJ (US)

(73) Assignee: Kalaco Scientific, Inc., Scottsdale, AZ (US)

( * ) Notice: Subject to any disclaimer, the term of this patent is extended or adjusted under 35 U.S.C. 154(b) by 697 days.

(21) Appl. No.: 11/820,844

(22) Filed: Jun. 19, 2007

(65) Prior Publication Data

US 2008/0319492 A1    Dec. 25, 2008

(51) Int. Cl.
    A61N 1/34    (2006.01)
(52) U.S. Cl. .............................. 607/46; 607/48; 607/66; 607/68; 607/74; 607/148
(58) Field of Classification Search .................... 607/46, 607/48, 68, 74, 139
    See application file for complete search history.

(56) References Cited

U.S. PATENT DOCUMENTS

| | | |
|---|---|---|
| 309,897 A | 12/1884 | Thurston |
| 693,257 A | 2/1902 | Gavigan |
| 3,893,463 A | 7/1975 | Williams |
| 4,014,347 A | 3/1977 | Halleck et al. |
| 4,541,432 A | 9/1985 | Molina-Negro |
| 4,729,377 A | 3/1988 | Granek |
| 4,793,353 A | 12/1988 | Borkan |
| 4,841,973 A | 6/1989 | Stecker |
| 4,856,525 A | 8/1989 | van den Honert |
| 5,254,081 A | 10/1993 | Maurer |
| 5,476,481 A * | 12/1995 | Schondorf ...................... 607/2 |
| 5,941,906 A | 8/1999 | Barreras, Sr. et al. |
| 6,553,253 B1 | 4/2003 | Chang |

(Continued)

FOREIGN PATENT DOCUMENTS

EP    0171881 A1    2/1986

(Continued)

OTHER PUBLICATIONS

Notification of Transmittal of the International Search Report and The Written Opinion, The International Search Report and The Written Opinion dated Mar. 25, 2009 in corresponding International Patent Application No. PCT/US2008/007518 filed Jun. 16, 2008 entitled "Multi-Channel Electrostimulation Apparatus and Method", 10 pages.

(Continued)

*Primary Examiner*—Carl H Layno
*Assistant Examiner*—Luther G Behringer
(74) *Attorney, Agent, or Firm*—Lewis and Roca LLP

(57) ABSTRACT

A therapeutic electrostimulation apparatus and method operates to supply electrostimulation signals to three channels. The basic electrostimulation signal for each of the channels is the same; and this signal is applied to a transcranial electrostimulation set of output electrodes. A second channel provided with the same signal is further operated to modulate the signal with a dual frequency signal pattern for the application of the second channel signal to a second set of electrodes, typically applied to the body near the spinal area. A third channel supplied with the basic electrostimulation signal modulates the electrostimulation signal during a portion of a treatment session with a diapason of frequencies varying randomly, and the output of this channel is applied to a set of electrodes at a local area for therapeutic treatment.

12 Claims, 3 Drawing Sheets

U.S. PATENT DOCUMENTS

| | | |
|---|---|---|
| 6,684,106 B2 | 1/2004 | Herbst |
| 6,904,322 B2 | 6/2005 | Katsnelson |
| 6,909,917 B2 | 6/2005 | Woods |
| 6,944,503 B2 | 9/2005 | Crowe |
| 7,127,287 B2 | 10/2006 | Duncan |
| 2005/0278001 A1 | 12/2005 | Qin |
| 2006/0259099 A1 | 11/2006 | Goetz |

FOREIGN PATENT DOCUMENTS

| | | |
|---|---|---|
| EP | 1181949 A2 | 2/2002 |
| EP | 1502623 A1 | 2/2005 |

OTHER PUBLICATIONS

Limoge A. et al., "Transcutaneous cranial electrical stimulation (TCES): A Review 1998," Neuroscience and Behavioral Reviews, Jan. 1, 1999, vol. 23, No. 4, pp. 529-538 (XP002265735), Pergamon Press Ltd. (Category A document; pp. 1-4 relevant to claims 1-12.).

Supplementary Search Report and Annex to Supplementary Search Report dated May 10, 2010 in corresponding European Patent Application No. 08 779 662.9 entitled Multi-channel Electrostimulation Apparatus and Method, 2 pages.

* cited by examiner

MULTI-CHANNEL ELECTROSTIMULATION APPARATUS AND METHOD

BACKGROUND

Bio-electric stimulation apparatus has been developed for applying current pulses to a patient through electrodes located on opposite sides of the head of the patient. The current pulses at selected frequencies are applied to cause reaction with the central nervous system of the patient. Such devices, referred to as transcranial electrostimulation (TCES) or cranial electrostimulators (CES) have been used for a variety of non-invasive procedures, such as producing analgesic effects, reducing or controlling migraine headaches, and other applications of treatment and electro-anesthesia.

Earliest prototypes of transcranial electrostimulation devices originated in Russia. These original designs, although successfully employed for several different treatment modalities, had a severe drawback with regard to the comfort of the wearer or patient. In some cases, these earlier cranial electrostimulation devices even subjected the wearer to pain. It has been discovered that the reason for the discomfort of these earlier designs was a result of the use of direct current as part of the overall operation of the devices. The direct current was used to break down or lower skin resistance to allow the treatment alternating current signals to penetrate the brain and nervous systems to cause the desired effect established by the placement of the electrodes on the head of the patient.

In these earlier types of machines, the wearer received a combination of direct current and alternating current electrical waveform packages through a series of electrodes affixed to the head with straps. Typically, two electrodes comprising a cathode or negative pole of the DC based circuit would be placed approximately three inches apart to the left and right of the center of the forehead. Two other electrodes, comprising the anode or positive pole of the DC based circuit, were placed on the rear of the skull on the post mandibular area behind and below each ear.

With this DC current based design, the wearer was required to place a thick pad between any electrode and the skin. Typically, the pad was comprised of several layers of unbleached and uncolored cotton flannel, or an equivalent product. For best results, the fabric pads were soaked with water to provide a conductive path between the electrodes and the skin of the wearer. Without the presence of the pads (which were only required because of the presence of the DC current), such devices could either burn the skin of the wearer, or cause relatively intense pain before a usable level of the treatment modality of the currents at the AC frequency could be reached.

Although various types of treatment were employed by such earlier transcranial electrostimulation devices, the devices typically needed to be employed for an average time of thirty minutes per treatment period. Without the presence of the relatively thick cumbersome pads, the DC based design was unusable. With the presence of the thick padding, the DC design was bearable to the wearer, but rarely provided the wearer with a pleasant experience.

Three Russian patents which utilize such devices for different treatment methods comprise Russian patent Nos. 1489719; 1507404; and 1522500. In all of these patents, a combination of direct current and rectangular impulse current, with a frequency of between 70 and 80 Hertz, was employed at current amperages which were increased from a relatively low level to a higher or maximum level over the course of each treatment session.

An additional and potentially harmful drawback of the DC based designs was that of iontophoresis. A characteristic of a DC circuit application of this type is that molecular sized parts of metal, toxins and other undesirable impurities can be caused to migrate in the direction of current flow through the skin and into the bloodstream of the wearer of such DC based CES devices. Consequently, care had to be taken to ensure that no substance was present other than water used to create good electrical contact with the pad to the skin of the wearer. Since practically all CES treatment modalities require repeated treatments, the potential for iontophoresis being a harmful factor was escalated.

Transcranial electrostimulation (CES or TCES) originally was used in the 1960's to induce sleep. These early devices typically used less than 1.5 mA at 100 Hz. The Liss U.S. Pat. No. 4,627,438 employed higher frequencies modulated by a lower frequency squarewave to produce recurring pulse bursts. The repetition frequency of the device of Liss is determined by the modulation frequency; but the pulse bursts are of a uniform amplitude within each repetition cycle. The device of the Liss patent is specifically directed to utilization in conjunction with the treatment of migraine headaches. The low frequency or modulating signal is asymmetrical, utilizing a 3:1 duty cycle, "on" three-fourths of the time and "off" one fourth of the recurring period. This results in bursts of the high frequency signal separated by the off time when no signal is applied, following the re-application of the bursts of the high frequency signal. Some patient discomfort may be present in such an "on/off" system operation over the period of time of application of the pulse during a treatment interval.

A number of other United States patents, all directed to dual frequency systems which utilize high frequency signals modulated by a low frequency modulation carrier, operating in the general nature of the device of the Liss U.S. Pat. No. 4,627,438, exist. Typical of these patents are the patents to Limoge U.S. Pat. No. 3,835,833; Nawracaj U.S. Pat. No. 4,071,033; Kastrubin U.S. Pat. No. 4,140,133; Morawetz U.S. Pat. No. 4,922,908 and Giordani U.S. Pat. No. 5,131,389. All of these patents employ a uniform amplitude high frequency signal, which is modulated at the lower frequency of the modulation carrier.

A variation on the systems of the patents discussed above is disclosed in the Haimovich U.S. Pat. No. 5,540,736. The device of this patent employs two different current generators for providing electrical currents delivered to two electrode pairs operating across different portions of the head of the patient. This allows independent control of the current generators to administer independent regulated electrical current across each of the pairs to adjust for different impedances caused by the physiological and anatomical differences between different sides of a patient's mid brain portion, the quality of the conducting medium, and other factors. In all other respects, the system disclosed in this patent is similar to the operation of the system disclosed in the Liss patent discussed above.

Russian patent publication No. 2139111 is directed to a method for treating narcomania, which is a treatment also used in others of the CES patents described above for alcohol and narcotic addiction. In this patent, transcranial electrical stimulation is accomplished by means of packets of current with a duration of four milliseconds, at a modulation frequency of 100 Hz. Within each of the packets, the high frequency signals have a uniform frequency and current amplitude.

The Katsnelson U.S. Pat. No. 6,904,322 is directed to a transcranial electrostimulation apparatus which employs an asymmetrical signal modulated by a 77.5 Hz modulating signal, with a resultant lowering of the capacitive resistance of the epidermal layer. As a consequence, lower current levels using the Katsnelson system of the '322 patent were found capable of achieving the desired results which previously required much higher current levels. The lower current levels of this system translate into a greater level of comfort for the patient or user of the device of the Katsnelson patent.

There also have been a number of efforts in the past to apply electrical signals to multiple body sites, in an effort to obtain some type of therapeutic result, such as pain relief. Early efforts, such as disclosed in the Phurston U.S. Pat. No. 309,897 and Gavigan U.S. Pat. No. 693,257, apply direct current to pads located at different locations on the body. These devices are subject to the same disadvantages described above for direct current TCES and CES systems, inasmuch as a relatively high level of discomfort or pain may be experienced through the use of direct current applications. Other devices employing stimulation of electrodes applied to the skin or external areas of the body, or implanted in permanent locations for therapeutic purposes, have been devised using alternating current signals. Such devices, however, have not been coordinated or combined with the use of transcranial electrostimulation apparatus, or cranial electrostimulators.

It is desirable to provide a system which combines transcranial electrostimulation with therapeutic stimulation to other body locations utilizing coordinated signals between the transcranial electrostimulation apparatus and the other applications to improve the efficacy of the treatment, and to obtain increased user comfort.

DETAILED DESCRIPTION

Figure 1:
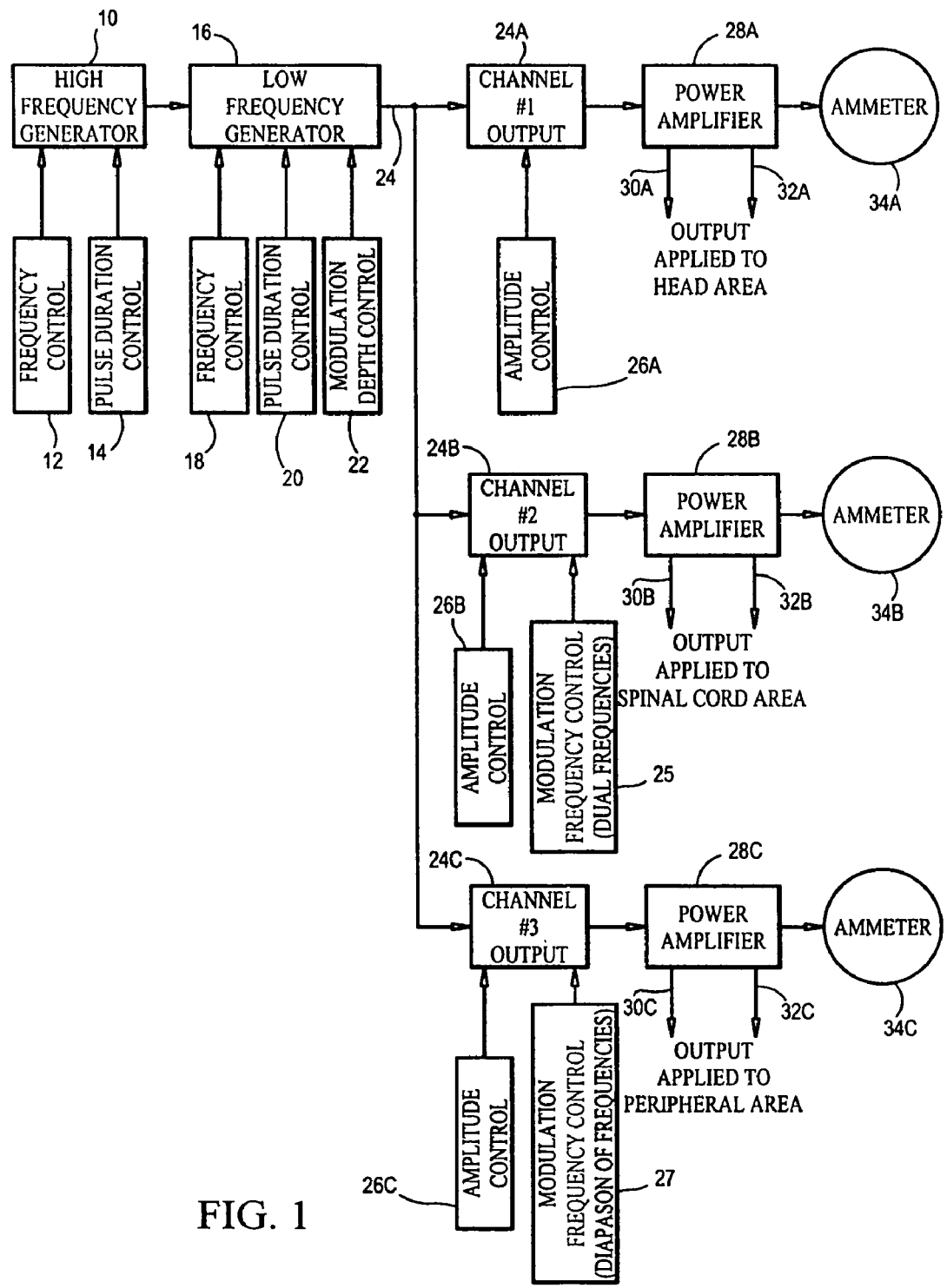
FIG. 1 is a diagrammatic drawing illustrating the overall principles of operation of the system in accordance with an embodiment of the invention.

Reference now should be made to the drawings which illustrate an embodiment of the invention and its operation. FIG. 1 is a diagrammatic representation of the salient operating features of circuitry implementations which produce a unique triple waveform asymmetry useful for various transcranial electrostimulation applications combined with simultaneous electrostimulation applications to other portions of human anatomy for maximum therapeutic efficacy. The waveform which is described in detail in conjunction with FIG. 2 produces little to no discomfort to the user of the device when applied to the head area for transcranial electrostimulation, and similarly, produces little or no discomfort when applied to other areas of the anatomy, as subsequently described.

As illustrated in FIG. 1, the basic high frequency current signals are produced by a high frequency generator 10, which may employ a frequency control 12 and a pulse duration control 14 to establish the basic frequency and to provide the desired asymmetry between the positive and negative portions of each of the pulses produced by the generator 10. Typically, the generator 10 may include a crystal oscillator operating at 1,000 to 1,200 kHz, which then is divided down to the desired operating frequency of the alternating current signal pulses applied to the transcranial stimulation electrodes and to additional electrodes applied to the spinal cord area, and to a peripheral pain area, such as a knee, elbow or the like. Typically, the division ratio may be a 1:4 ratio to produce signals which then are modulated by a low frequency generator 16.

As illustrated in the diagrammatic representation of FIG. 1, the output of the low frequency generator 16 may be established by means of a conventional frequency control 18, a pulse duration control 20, and a modulation depth control 22 to produce a composite modulated output signal at 24. The signal 24, which comprises the pulses from the output of the high frequency generator 10 modulated by the low frequency generator 16 then is provided to three different channel outputs 24A, 24B and 24C.

Each of the channel outputs is further provided with a corresponding amplitude control 26A, 26B and 26C, respectively, to establish the amplitude of the pulse train supplied to the system through three corresponding power amplifiers 28A, 28B and 28C, respectively. The current at each of these power amplifiers 28A, 28B and 28C may be varied in accordance with the treatment modality to be used by the system; and this current is measured by the respective ammeters 34A, 34B and 34C. The various power amplifiers 28A, 28B and 28C then supply the appropriate alternating current pulses to multiple pairs of electrode outputs, illustrated as pairs 30A/32A; 30B/32B; and 30C/32C in FIG. 1. As indicated in FIG. 1, the electrode outputs 30A/32B are applied to the head area, or for transcranial electrostimulation; the electrodes 30B/32B are applied to the spinal cord area of a human anatomy; and the electrodes 30C and 32C are applied to a peripheral area of a human anatomy, as mentioned above.

It also should be noted in the circuit of FIG. 1 that in addition to the amplitude control, the channel 2 output 24B also is further modulated by a modulation frequency control 25 of dual frequencies. Similarly, the channel 3 output 24C is additionally controlled by a modulation frequency control 27, which applies a diapason of modulation frequencies to the channel 3 output. The result is that while the three-channel outputs from the channel outputs 24A, 24B and 24C all are supplied with an identical signal from the low frequency generator 16, the outputs are not identical when they are finally applied to the respective power amplifiers 28A, 28B and 28C to the corresponding output electrodes. The variations are made by the modulation frequency control circuits 25 and 27, which are coupled with the channel 2 output 24B and channel 3 output 24C, respectively.

The operation of the disclosed embodiment of the invention produces a waveform having triple asymmetry in order to produce effective transcranial stimulation and further effective stimulation to the spinal cord area and to a peripheral body area, such as an elbow, knee, finger, or the like. The waveform of FIG. 2 and the block diagram of the system shown in FIG. 3 further illustrate the nature of the signals, and the manner in which these signals are processed. The block diagram of the system shown in FIG. 3 is typical of the manner of implementation of the various circuit functions required to produce the waveform of FIG. 2; but other arrangements for producing the signal waveform also may be utilized.

Figure 2:
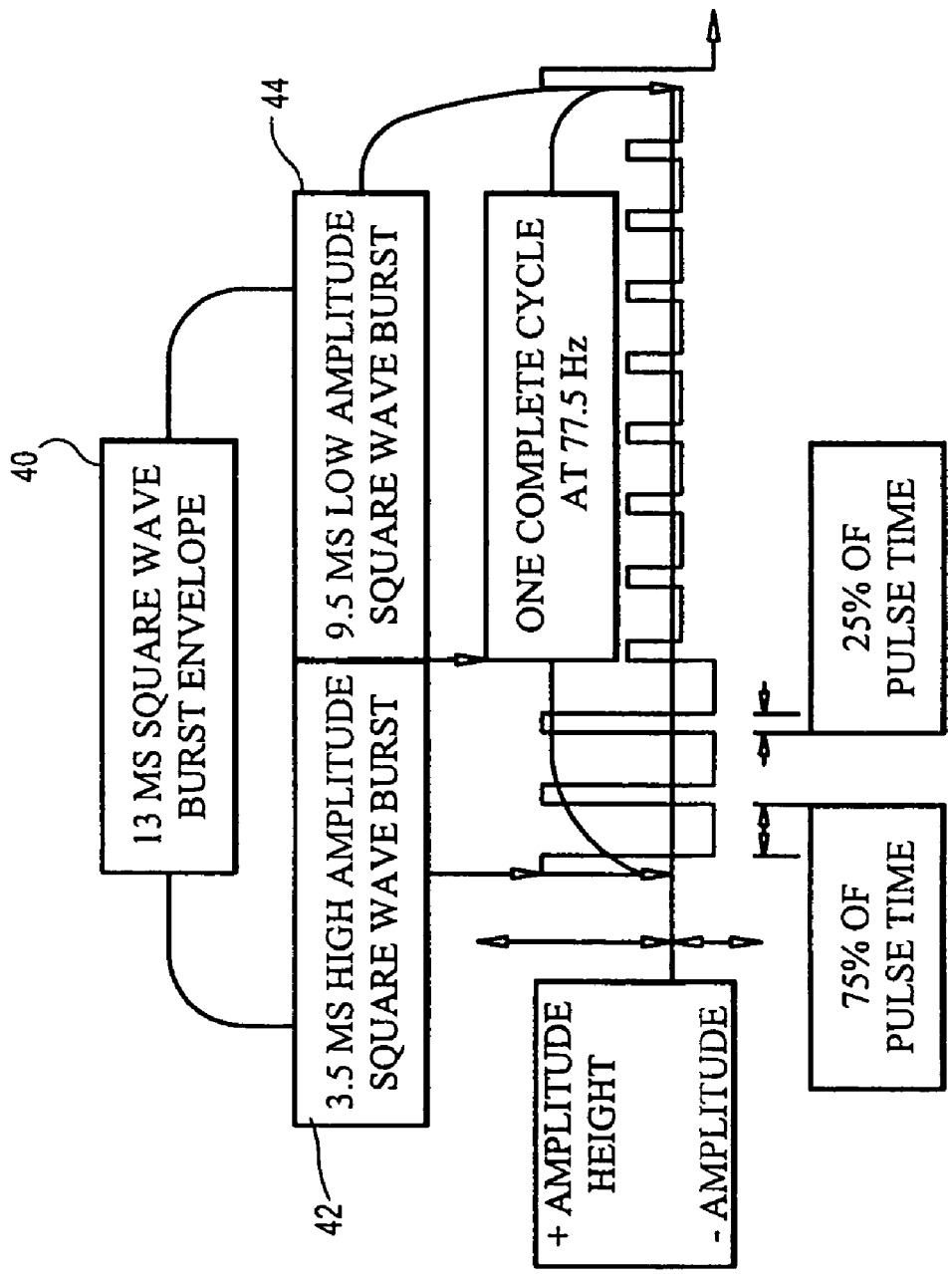
FIG. 2 is a waveform of a typical signal pattern of an embodiment of the invention.
Figure 3:
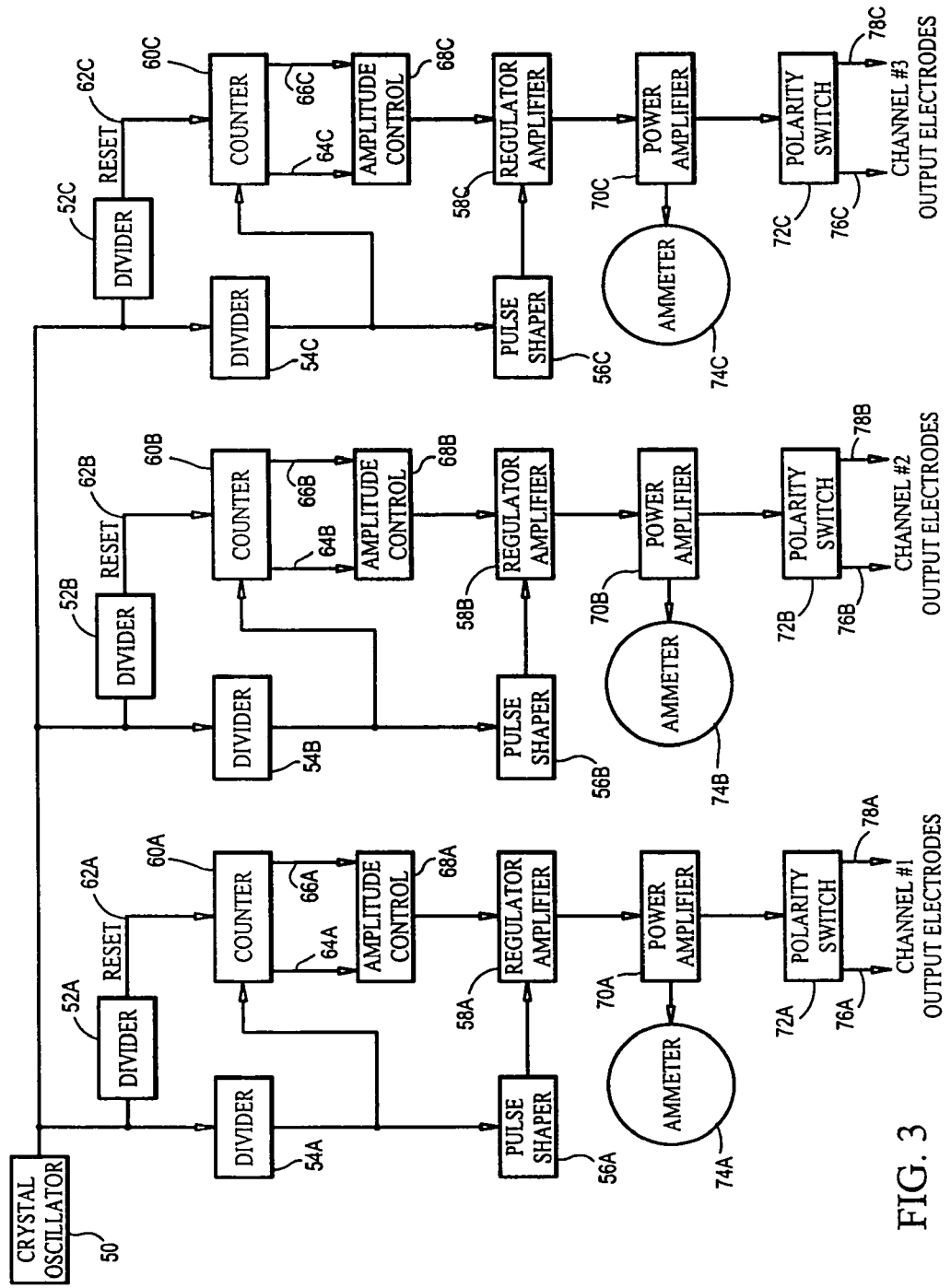
FIG. 3 is a block diagram illustrating additional details of the system of the embodiment of the invention shown in FIGS. 1 and 2.

In FIG. 3, a crystal oscillator 50 is employed to provide the basic alternating current operating signals utilized for both the high frequency pulses and the modulating pulses, illustrated in FIG. 1 as being produced by the high frequency generator 10 and the low frequency generator 16, respectively. Typically, the oscillator 50 may have an operating frequency in the order of 1,000 kHz to 1,200 kHz (although other frequencies may be used). In FIG. 3, the output of this oscillator is supplied in parallel to three dividers 52A, 52B and 52C, which each may comprise multiple division stages, to produce the lower modulating frequency (illustrated in FIG. 1 as being generated by the low frequency generator 16). The output signals from the oscillator 50 also are supplied in parallel through three frequency dividers 54A, 54B and 54C to produce the operating signal waveform shown as the squarewave signal in the waveform of FIG. 2, after being shaped by a pulse shaper 56A, 56B and 56C, respectively, to achieve the generally squarewave configuration of the signal shown in FIG. 2. In the example given, these pulses occur at an alternating current rate of 100 KHz; although they could be at higher or lower frequencies in accordance with particular applications of the system.

The pulses from the output of the dividers 54A, 54B and 54C are respectively supplied to counters 60A, 60B and 60C, which may be of any suitable type such as a cascade counter or a ring counter, for producing outputs on sets of leads 64A/66A; 64B/66B; and 64C/66C, respectively, utilized in controlling the amplitude of the pulses from the corresponding pulse shapers 56A, 56B and 56C. The counters 60A, 60B and 60C are reset by the outputs of their respective dividers 52A, 52B and 52C, applied over the respective leads 62A, 62B and 62C, to reset the counters 60A, 60B and 60C for each cycle of operation of the corresponding dividers 52A, 52B and 52C. In the present example, the output of the dividers 52A, 52B and 52C (comprising the low frequency modulation control signal described previously in conjunction with FIG. 1) is selected to be 77.5 Hz, since this repetition frequency has been found to be highly effective in conjunction with transcranial electrostimulation devices. Repetitive frequencies which are in the range of 70 Hz to 85 Hz have been found to be effective, but a frequency of 77.5 Hz has been empirically ascertained as a general ideal operating frequency for producing the maximum efficacy of the system, particularly for the transcranial electrostimulation, which takes place from the channel 1 output electrodes 30A/32/A applied to the head area of a person.

The modulating or reset frequency, applied over the leads 62A, 62B and 62C, could as well be supplied by a second independent crystal oscillator, operating at a lower initial frequency than the frequency of the oscillator 50, if desired. If two different signal sources are employed, synchronization between the two should be effected to cause the various pulse transitions of the signals to be correlated with one another in order to produce the signal waveform of FIG. 2. The system shown in FIG. 3, however, is an effective way of accomplishing this purpose.

Assume, for the present example, that the counter 60A has been reset to its initial or "zero" count. The system then operates to supply output pulses at the high frequency of the divided down signal from the divider 54A to the counter input, which advances one count for each of the applied pulses. In the waveform shown in FIG. 2, the initial pulses (the first four in FIG. 2) cause the counter outputs on 64A and 66A to be such that, as these outputs are applied to the amplitude control 68A, a maximum amplitude (which may be adjusted if desired) is produced. This is illustrated in the left-hand portion of the waveform signal of FIG. 2.

When pulse No. 4 in the group or packet of pulses is applied, a signal is obtained from one or both of the outputs 64A and 66A of the counter 60A and applied to the amplitude control circuit 68A to switch it to a lower amplitude, as illustrated for the right-hand portion of the signal shown in FIG. 2. This causes the output of the amplitude control circuit 68A, as applied to a regulator amplifier 58A, to produce the signal waveforms in the asymmetrical pattern shown in FIG. 2, wherein the left-hand one-fourth (42) of each of the signal burst envelopes 40 is at a high amplitude; and the right-hand portion (44) comprising the remainder of the pulses in the burst envelope 40 is at a lower amplitude. The ratio is such that one-fourth (the initial amplitude) is at the high amplitude range 42, and that the remainder three-fourths of the signal burst is at the low amplitude range 44. This is the first level of asymmetry of the applied signals.

The regulator amplifier 58A also operates on the squarewave shaped pulses from the pulse shaper 56A to cause a second asymmetry in the positive and negative going aspects of the signal. As shown in FIG. 2, the negative going amplitude is one-fourth of the total excursion of the signal; and the positive going portion is three-fourths of the total excursion. This is true of both the maximum amplitude pulse burst 42 at the beginning of each of the burst groups or packets, and the lower amplitude portion 44 at the end of each of the burst groups or envelopes.

Finally, a third asymmetry is produced within the thirteen millisecond squarewave burst envelope illustrated as 40 in FIG. 2. This is the result of the operation of the divider signal on the lead 62A comprising the reset operation for the counter 60A. The pulse time, or dwell time, for the positive-going aspect of the signal is one-fourth of the total pulse width; while the pulse time for the negative-going aspect of the signal is three-fourths of the total pulse width.

The composite asymmetrical signal illustrated in FIG. 2 then is provided by the output of the regulator amplifier 58A to a power amplifier 70A. The amplification may be adjusted to change the amount of current applied by the system (while maintaining the relative waveform shapes and patterns shown in FIG. 2) in accordance with the treatment modality to be utilized by users of the system. The ammeter 74A is employed to measure the magnitude of the current supplied by the system. The ammeter 74A may be a simple analog ammeter, or it may be a digital ammeter providing separate readings of the maximum amplitude and minimum amplitude portions of the signal which is shown in FIG. 2.

The output of the amplifier 70A may be applied through a polarity switch 72A which allows the polarity of the signals applied to the output electrodes to be reversed, if desired. The polarity switch 72A supplies the signals across a pair of spaced output electrodes 76A and 78A which may be in the form of pairs of split anodes and split cathodes, or which may be a single "anode" and "cathode" pair, or any combination thereof. These are the electrodes which are applied to the head area of the user for transcranial electrostimulation. Since no direct current components are present, the electrode paths connected to the outputs 76A and 78A are not really anodes and cathodes; but, depending upon the treatment which is being effected, it may be desirable to apply the positive going portions of the pulses to one or the other of these electrodes and the negative going portions to the other of the two electrodes 76A and 78A to achieve specific results.

It should be noted that in the system which is shown and described, there are no direct current components. It also should be noted that although the system essentially is illustrating 70 kHz to 120 kHz tone bursts in each of the burst envelopes 40 shown in FIG. 2, other frequencies could be employed. The 77.5 Hz waveform derived through the timing cycle is used to complete each burst envelope 40 including first pulses of a relatively high amplitude, followed by a series of pulses of relatively low amplitude in accordance with the signal pattern shown in FIG. 2. The frequency of pulses comprising the asymmetrical tone burst is approximately 1,150 to 1,450 times the repetition frequency of the burst envelopes 40.

In the system which is described above, an individual squarewave pulse of 0.01 Ms is utilized with 0.0075 Ms in the negative portion of the pulse and 0.0025 Ms in the positive portion of each of the pulses. The general asymmetrical waveform which is described above in conjunction with FIG. 2 has been found to be effective when it is centered around three-to-one ratios throughout the system operation. These ratios of course may be varied, in accordance with corresponding variations of other ratios of the system; but it has been found that the asymmetrical relationship which is disclosed replaces the formerly necessary, but unpleasant, DC portion of the operating protocol of earlier systems.

It has been found that the utilization of the unique asymmetrical signal produced by the system shown in FIG. 3 and illustrated in the waveform of FIG. 2 effectively lowers the capacitive resistance of the epidermal layer to something on the order of 100 Ohms. Since less resistance is presented to the integrated 77.5 Hz modulating frequency, lower current levels are capable of achieving the same desired result which previously required much higher current levels. The lower current levels translate into a greater level of comfort for the patient or user of the device.

The signals supplied to the channel 2 and channel 3 outputs, illustrated as 24B and 24C of FIG. 1, are processed through essentially identical circuitry in FIG. 3, with the exception that in conjunction with the channel 2 output 52B through 78B and the channel 3 output 52C through 78C, the additional modulation which is indicated as applied by the modulators 25 and 27 (FIG. 1), respectively, for the number 2 and number 3 channel outputs is employed. In all other respects, the operation of these additional channels employs the same basic signal shown in FIG. 2 and described above in conjunction with FIG. 1.

In conjunction with channel 2, the power amplifier 70B is provided with an additional or second modulation frequency control by the modulator 25 shown in FIG. 1, coupled to the power amplifier 70B in any suitable manner. The additional modulation frequency switches between two frequencies in the range of 0.01 Hz and 100 Hz. Two empirically chosen frequencies of 7.75 Hz and 77.5 Hz for modulating the signal pattern of the signal bursts of FIG. 2, have been found to produce satisfactory results. These modulation frequencies each are applied for a relatively long period of time, on the order of thirty to forty minutes during a treatment session. The system starts with the modulation frequency of 77.5 Hz applied by the modulator 25, which then is followed, after an appropriate interval, typically one-half of the session duration, with the lower modulating frequency of 7.75 Hz for a similar length of time. The switching between the two modulating frequencies continues from the higher frequency to the lower frequency, and back again, over a therapy session, which typically lasts on the order of thirty to forty minutes. The output electrodes 76B and 78B (or 30B and 32B of FIG. 1) of channel 2 are applied to different locations on the back vertebrae, typically at the lower back. The amplitude of the channel 2 current ranges up to 150 mA.

The Channel 3 portion of the system, indicated from the divider 52C through the output electrode 78C, also is supplied with the signal of FIG. 2 in the same manner as that signal is applied to the channel 1 and channel 2 portions of the system. The channel 3 output electrodes 76C and 78C (or 30C and 32C of FIG. 1) are used for peripheral stimulation. For example, if the therapeutic treatment is for pain in a knee or an elbow, the electrodes are placed across the appropriate areas for treatment. The signal frequency applied to the dividers 52C and 54C is obtained, as described above in detail for channel 1. The 77.5 Hz signal burst envelopes 40 are then further modulated with a third modulation frequency within a diapason of frequencies (typically between 0.01 Hz and 10 Hz). A range from 7.75 Hz to 0.775 Hz has been found effective. The basic modulation is 77.5 Hz, as with the modulating frequency for channel 1, and as with one of the modulating frequencies for channel 2 (52B through 78B). The depth of the modulations is the same as used for channel 1 (52A through 78A).

The starting frequency for channel 3 is selected to be 77.5 Hz, for the first portion of a treatment session, with the diapason frequencies of 7.75 Hz to 0.775 Hz then continuing for the second portion of a treatment session. As with channel 2, the channel 3 current amplitude ranges up to 150 mA. A typical treatment session lasts between thirty minutes and forty minutes. For such a treatment session, the frequency of modulation for the burst envelope for channel 1 is 77.5 Hz continuously, throughout the session. For channel 2, the modulation frequency for the first half of the session (15 or 20 minutes, depending upon the session length) is at 77.5 Hz. During the second half of each treatment session, the modulating frequency for channel 2 drops to 7.75 Hz. For channel 3, the modulation frequency during the first half of the treatment session is the basic 77.5 Hz frequency; but during the second half of the treatment session, the modulating frequency for channel 3 switches to a frequency in the diapason of 7.75 Hz to 0.775 Hz for the remainder of the second half of the session. The frequency changes in this diapason are randomly changed every two or three minutes. This typically completes a treatment session. For some situations, however, the entire session may be repeated, with everything going "back again" to the starting conditions mentioned above, and then repeating the operation described.

The application of the signal of FIG. 2 to the three channels (with the additional modulation described for channels 2 and 3) used together with the 3 output electrode sets results in improved therapeutic relief over that which is obtained from TCES (channel 1) used alone. A synergism of the three signals appears to produce more lasting beneficial results.

The foregoing description of an embodiment of the invention is to be considered as illustrative and not as limiting. Various changes and modifications will occur to those skilled in the art for performing substantially the same function, in substantially the same way, to achieve substantially the same result without departing from the true scope of the invention as defined in the appended claims.

What is claimed is:

1. A therapeutic electrostimulation apparatus for use in a treatment session having first and second portions, the apparatus including in combination: a source of bipolar pulses of a first predetermined frequency; first, second and third amplitude control circuits each having an input and each having an output, with the inputs of the first, second and third amplitude control circuits coupled to the source of bipolar pulses at the first predetermined frequency; a first source of modulating control signals to yield a first modulating frequency which is less than the first predetermined frequency; a second source of modulating control signals to yield modulating frequencies at the first modulating frequency and a second modulating frequency; a third source of modulating control signals to yield modulating frequencies at the first modulating frequency and within a diapason of third modulating frequencies; the first source of modulating control signals coupled with the first amplitude control circuit to cause the amplitude of bipolar pulses in successive groups of bipolar pulses to vary in accordance with a predetermined asymmetrical pattern at the first modulating frequency throughout the first and second portions of a treatment session; a first set of output electrodes coupled with the output of the first amplitude control circuit for use as transcranial electrostimulation output electrodes; the second source of modulating control signals coupled with the second amplitude control circuit for modulating the output of the second amplitude control circuit with the first modulating frequency during the first portion of a treatment session and with the second modulating frequency during the second portion of a treatment session; a second set of output electrodes coupled with the output of the second amplitude control circuit for use as spinal cord electrostimulation output electrodes; the third source of third modulating control signals coupled with the third amplitude control circuit for modulating the output of the third amplitude control circuit with the first modulating frequency during the first portion of a treatment session and with frequencies within the diapason of third modulating frequencies during the second portion of a treatment session; and a third set of output electrodes coupled with the output of the third amplitude control circuit for use as peripheral area electrostimulation output electrodes.

2. The apparatus according to claim 1 wherein each of the amplitude control circuits causes the bipolar pulses to have a greater amplitude in a first portion of each group of pulses and to have a lesser amplitude in a second portion of each group of pulses.

3. The apparatus according to claim 2 wherein the amplitude of the pulses in the first portion of each group of pulses has an amplitude substantially three times the amplitude of the pulses in the second portion.

4. The apparatus according to claim 3 wherein the first and second modulating frequencies are 77.5 Hz and 7.75 Hz, respectively.

5. The apparatus according to claim 4 wherein the frequencies within the diapason of third modulating frequencies vary in a random pattern.

6. The apparatus according to claim 3 wherein the first modulation frequency is between 70 Hz and 85 Hz.

7. The apparatus according to claim 1 wherein the first and second modulating frequencies are 77.5 Hz and 7.75 Hz, respectively.

8. The apparatus according to claim 7 wherein the frequencies within the diapason of frequencies vary in a random pattern.

9. The apparatus according to claim 1 wherein the first modulation frequency is between 70 Hz and 85 Hz.

10. The apparatus according to claim 1 wherein the frequencies within the diapason of frequencies vary in a random pattern.

11. The apparatus according to claim 10 wherein the amplitude control circuits cause the bipolar pulses to have a greater amplitude in a first portion of each group of pulses and to have a lesser amplitude in a second portion of each group of pulses.

12. The apparatus according to claim 11 wherein the amplitude of the pulses in the first portion of each group of pulses has an amplitude substantially three times the amplitude of the pulses in the second portion.

* * * * *